United States Patent [19]

Grüning et al.

[11] Patent Number: 5,124,446
[45] Date of Patent: Jun. 23, 1992

[54] BETAINE GROUP-CONTAINING POLYSACCHARIDES WITH RECURRING ANHYDROGLUCOSE UNITS, THEIR SYNTHESIS AND THEIR USE IN COSMETIC PREPARATIONS

[75] Inventors: Burghard Grüning; Klaus Hoffmann; Götz Koerner; Hans-Joachim Kollmeier, all of Essen, Fed. Rep. of Germany

[73] Assignee: Th. Goldschmidt AG, Essen, Fed. Rep. of Germany

[21] Appl. No.: 353,349

[22] Filed: May 17, 1989

[30] Foreign Application Priority Data

Jun. 13, 1988 [DE] Fed. Rep. of Germany ....... 3820030

[51] Int. Cl.$^5$ .................... C07H 15/00; C07H 1/00; A61K 7/06
[52] U.S. Cl. .................... 536/120; 536/119; 536/17.9; 536/17.2; 536/124; 514/880; 514/881; 424/70
[58] Field of Search ............ 536/120, 119, 17.9, 536/17.2, 124; 514/880, 881; 424/70

[56] References Cited

U.S. PATENT DOCUMENTS

| | | | |
|---|---|---|---|
| 3,472,840 | 10/1969 | Stone et al. | 536/31 |
| 3,654,261 | 4/1972 | Johnson | 536/17.9 |
| 3,931,148 | 1/1976 | Langdon | 536/17.9 |
| 4,767,463 | 8/1988 | Brode et al. | 424/70 |
| 4,772,689 | 9/1988 | Lang et al. | 424/70 |
| 4,822,598 | 4/1989 | Lang et al. | 424/70 |

FOREIGN PATENT DOCUMENTS

55-43165 3/1980 Japan .

Primary Examiner—Ronald W. Griffin
Assistant Examiner—Everett White
Attorney, Agent, or Firm—Akoo-Toren

[57] ABSTRACT

Betaine group-containing polysaccharides with recurring anhydroglucose units of the average, general formula

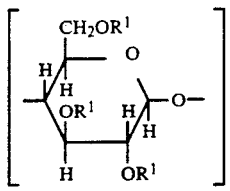

are disclosed. In this formula the $R^1$ groups are the same or different and represent methyl, $(C_nH_{2n}O)_mR^2$ or

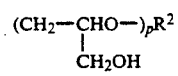

in which $n=2$ or 3, $m=0$ to 10, $p=0$ to 10 and $R^2$ is a hydrogen atom or the betaine group

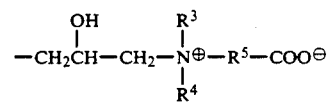

in which $R^3$ and $R^4$ are the same or different and represent an alkyl group with 1 to 4 carbon atoms and $R^5$ is a divalent aliphatic hydrocarbon group with 1 to 10 carbon atoms, with the proviso that at least 0.5% of the $R^1$ groups in the polysaccharide molecule represent the betaine group.

Also disclosed is a method for the synthesis of these compounds and their use in cosmetic preparations, especially for the care of the hair. In addition, novel compounds of the general formula

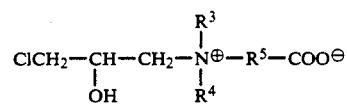

are disclosed as intermediates in which the substituents $R^3$, $R^4$ and $R^5$ have the above meaning.

14 Claims, No Drawings

BETAINE GROUP-CONTAINING POLYSACCHARIDES WITH RECURRING ANHYDROGLUCOSE UNITS, THEIR SYNTHESIS AND THEIR USE IN COSMETIC PREPARATIONS

FIELD OF INVENTION

The invention is directed to betaine group-containing polysaccharides with recurring anhydroglucose units, as well as to a method for the synthesis of these compounds and their use in cosmetic preparations, especially for the care of hair.

The invention furthermore is directed to compounds of the general formula

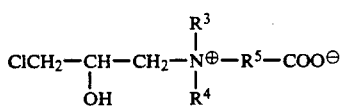   III in which $R^3$ and $R^4$ are the same or different and represent an alkyl group with 1 to 4 carbon atoms and $R^5$ is a bivalent aliphatic hydrocarbon group with 1 to 10 carbon atoms, as intermediates for the synthesis of betaine group-containing polysaccharides with recurring anhydroglucose units.

BACKGROUND INFORMATION AND PRIOR ART

Betaine group-containing derivatives of hydroxyethylcellulose are known from the art. However, these products do not have satisfactory properties when used in cosmetics, especially when used for the preparation of products for the care of hair. It is a further disadvantage of these products that, for their synthesis, reactants are used, which are not absolutely safe physiologically and the complete removal of which from the end product is not readily possible or requires measures, which make the economic use of the compounds impossible.

The Japanese published application 80-43 165 is named as belonging to this state of the art. This application claims amphoteric derivatives of hydroxyethylcellulose, these derivatives being characterized by at least 50 structural units of the general formula

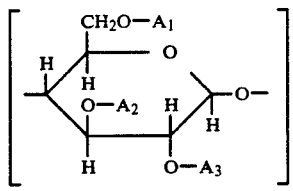

In this general formula
$A_1$ represents the group $-(C_2H_4O-)_pX_1$
$A_2$ represents the group $-(C_2H_4O-)_qX_2$
$A_3$ represents the group $-(C_2H_4O-)_rX_3$ $X_1$, $X_2$ and $X_3$ being either a hydrogen atom or an amphoteric group of the general formula

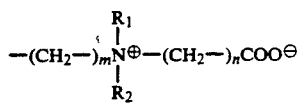

In this amphoteric group, $R_1$ and $R_2$ are a methyl or an ethyl group, m is a whole number from 1 to 6 and n is a whole number from 1 to 2, p, q and r=0 or a whole number not less than 1. The average number of moles of oxyethylene groups per structural unit is 0.5 to 3.0 and the average degree of substitution by amphoteric groups per structural unit is 0.02 to 1.0. It is evident from this description of the formula that the betainic group is linked over ether groups to the cellulose backbone.

Pursuant to the Japanese publication 80-43 165, these compounds are synthesized by, expressed in a simplified fashion, at first reacting an appropriate hydroxyethylcellulose with dialkylaminoalkyl halides of the general formula

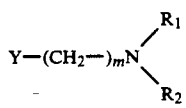

in the presence of alkali. In the above formula, Y is a halogen atom and the $R_1$ and $R_2$ groups and the m subscript have the above meaning. The intermediate obtained is then reacted with a monohalogencarboxylic acid or acrylic acid in the presence of alkali.

For various reasons, this method has proven to be disadvantageous. For instance, the dialkylaminoalkyl halide, used in the first step of the method, is an alkylating agent, which is not entirely safe physiologically and which should not remain in the product, especially if the end products are used in cosmetics. However, it is practically impossible to remove dialkylaminoalkyl halide quantitatively.

A further disadvantage consists therein that the tertiary amine, formed in the first step, reacts more readily with dialkylaminoalkyl halide than do the still unreacted hydroxyethyl groups of the hydroxyethylcellulose. In a side reaction, as a result of the addition reaction with a second dialkylaminoalkyl halide, this then leads to the formation of derivatives with quaternary amino groups, which are present in the end product next to the derivatives with betainic groups. Through the formation of these by-products, however, the compatibility of the products with anionic surfactants is reduced appreciably. This is of disadvantage in the application, since products for the care of hair in many cases contain anionic surfactants as well. The desired advantage in the application of the improved compatibility of compounds containing betaine groups is thus reduced or canceled.

Betaine group-containing derivatives of hydroxyethylcellulose are also disclosed, under certain assumptions, in the U.S. Pat. No. 3,472,840. In this U.S. Patent, a cellulose ether of the general formula

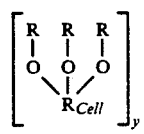

which contains a quaternary nitrogen, is claimed. The $R_{Cell}$ group is an anhydroglucose unit, y is a whole number with a value from 50 to 20,000 and each R represents a group of the general formula

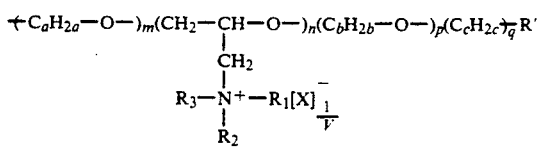

in which
a is a whole number with a value of 2 to 3,
b is a whole number with a value of 2 to 3,
c is a whole number with a value of 1 to 3,
m is a whole number with a value of 0 to 10,
n is a whole number with a value of 0 to 3,
p is a whole number with a value of 0 to 10,
q is a whole number with a value of 0 to 1,
R' is selected from a group consisting of

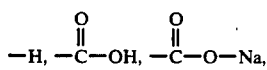

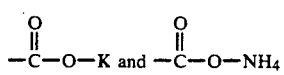

with the proviso that R'=H when q=0.

$R_1$, $R_2$ and $R_3$ in each case represent an alkyl, aryl, aralkyl, alkaryl, cycloalkyl, alkoxyalkyl or alkoxyaryl group with up to 10 carbon atoms. V is a whole number, which corresponds to the valence of X (to shorten it and to make it more understandable, some conditions have been disregarded in this citation).

In this U.S. Patent, the limiting case is mentioned that the anion X can be omitted totally or partly when R' is a carboxyl group, which forms an internal salt with the quaternary ammonium group. In this case, a betaine structure is present. If the anion X is displaced only partly, the disadvantages, inherent in products in which quaternary ammonium groups and betaine groups are present side by side, namely a poor or inadequate compatibility with anionic surfactants, may be observed once again. Cellulose derivatives, the structure of which corresponds to these handicaps, do not form clear aqueous solutions. Moreover, these compounds also do not have satisfactory properties, when they are used in the cosmetic area, especially in cosmetic preparations for the care of hair.

OBJECTS OF THE INVENTION

It is an object of the present invention to provide betaine group-containing polysaccharides with recurring anhydroglucose units, which can be used as thickening agents, as protective colloids and especially as active ingredients in cosmetic preparations for the care of hair and, at the same time, have improved hair-care properties. The products shall have an improved and, in any case, an adequate compatibility with anionic surfactants and show good solubility properties. More particularly, when used on hair, the new products shall bring about improved gloss, handle and combability. The substantivity of the products shall be so balanced, that any accumulation of the active ingredients on the hair, even after repeated application, is avoided.

SUMMARY OF THE INVENTION

It has now been found that betaine group-containing polysaccharides with recurring anhydroglucose units have this property profile, if, pursuant to the invention, they correspond to the average, general formula

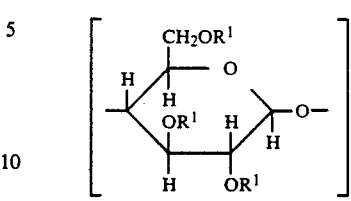

in which the $R^1$ groups are the same or different and represent methyl,

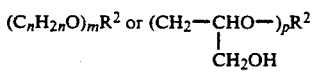

in which n=2 or 3, m=0 to 10, p=0 to 10 and $R^2$ is a hydrogen atom or the betaine group

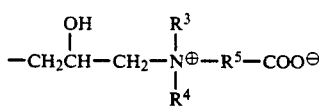

in which
$R^3$ and $R^4$ are the same or different and represent an alkyl group with 1 to 4 carbon atoms and
$R^5$ is a divalent aliphatic hydrocarbon group with 1 to 10 carbon atoms, with the proviso that at least 0.5% of the $R^1$ groups in the polysaccharide molecule represent the betaine group.

The $R^1$ groups within the anhydroglucose unit or within the polysaccharide constructed from these units may be the same or different. At least 0.5% of the $R^1$ groups must represent the betaine group II. Preferably, 5 to 20% of the $R^1$ groups are such betaine groups. Within the

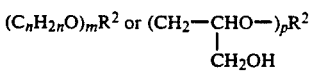

groups, n=2 or 3 and preferably 2, m=0 to 10 and preferably 0.3 to 3, and p=0 to 10 and preferably 0. In the betaine group II, $R^3$ and $R^4$ may be the same or different and represent an alkyl group with 1 to 4 carbon atoms. Preferably, they are methyl groups. $R^5$ is a divalent aliphatic hydrocarbon group with 1 to 10 carbon atoms. Examples of such divalent aliphatic hydrocarbon groups are

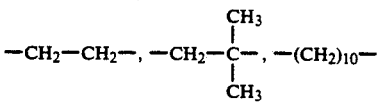

Preferably $R^5$ is $-CH_2-$.

Examples of groups, which have betaine groups and are linked to an anhydroglucose unit, are reproduced in the following formulas, in which R* stands for an anhydroglucose group, which optionally is partially substituted by methyl groups and which may originate from a polymer chain of cellulose or starch:

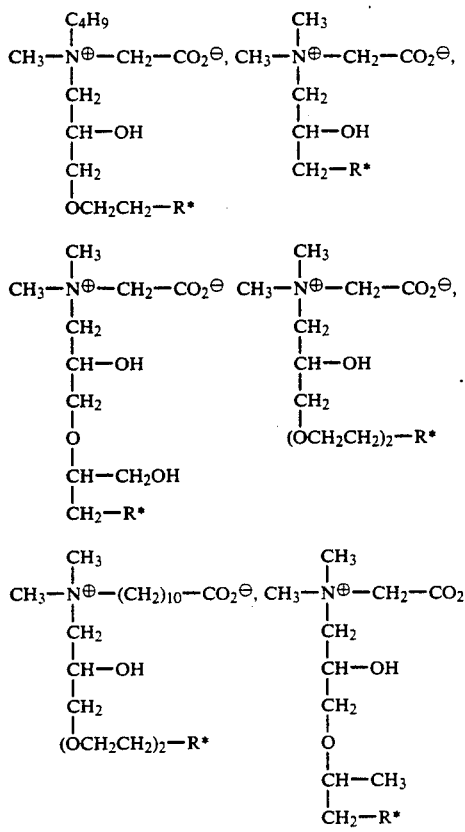

Depending on the type of bonds between the anhydroglucose units, the polysaccharides are either derivatives of starch (alpha glycosidic linkage) or of cellulose (beta glycosidic linkage). The derivatives of cellulose are preferred, as are the derivatives of hydroxyethylcellulose, that is, of those polysaccharides, in which a portion of the $R^1$ groups represent the $(C_2H_{2n}O)_mR^2$ group.

It is a further aspect of the invention to provide a method for the synthesis of the inventive compounds. This method is characterized in that polysaccharides with recurring anhydroglucose units of the average general formula

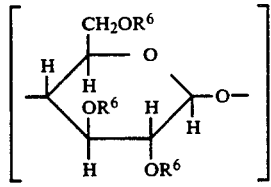

IV in which the $R^6$ groups are the same or different and represent $CH_3$,

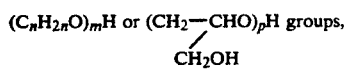

$(C_nH_{2n}O)_mH$ or $(CH_2-CHO)_pH$ groups, in which n, m and p have the above meaning with the proviso that not more than 70% of the sum of the $R^6$ groups may be methyl groups, are suspended in a polar organic solvent, which optionally contains water. At least 0.1 to 3 molar amounts of sodium hydroxide, based on anhydroglucose unit, are added to the suspension and the alkaline suspension is allowed to stand for 10 to 120 minutes at 0° to 30° C., and, if necessary, stirred, whereupon, based on the anhydroglucose units, 0.1 to 3 molar amounts of

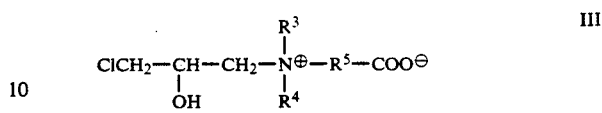

III dissolved in water or a polar organic solvent, which optionally contains water, are added. The reaction mixture is allowed to react at temperatures of 30° to 80° C. with stirring for 0.5 to 12 hours. When the reaction is completed, the product is isolated—with or without prior neutralization—by filtration, washing and drying.

It will be clear to those skilled in the art that, instead of the chlorohydrin of formula III, the epoxide derived therefrom and obtained by an alkaline treatment, can also be used in an equivalent manner.

Accordingly, for this method, the polysaccharides are first suspended in a polar organic solvent, which is at least partially miscible with water. As a polar organic solvent, lower aliphatic alcohols, ethers or ketones, such as isopropyl alcohol, tert.-butyl alcohol, dioxane, tetrahydrofuran, methyl ethyl ketone or acetone are advantageously used. Optionally, up to 20% water may be added to this polar organic solvent. The suspensions preferably contain 1 to 25% by weight solids. Sodium hydroxide is added to the suspension in amounts of at least 0.1 to 3 moles and preferably of 0.5 to 1.5 moles, based on the anhydroglucose unit. The sodium hydroxide is advantageously used in the form of a concentrated aqueous solution. The alkaline suspension, so obtained, is now allowed to stand for 10 to 120 minutes at 0° to 30° C., during which time the polysaccharide swells and is activated. To the suspension so prepared, a solution of the compound

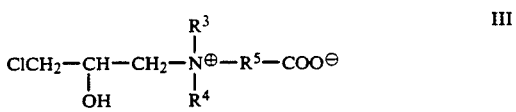

III in water or in a polar organic solvent, which optionally contains water, is added. For this purpose, the same organic solvent mentioned above is advantageously used. The reaction takes place over a period of 0.5 to 12 hours at a temperature within the range of 30° to 80° C. Preferably, the reaction time is 2 to 8 hours at a temperature of 40° to 60° C. During this time, the reaction mixture is preferably stirred. After the reaction, any excess of sodium hydroxide, which may be present, is preferably neutralized with an acid, preferably acetic acid, and the reaction product is filtered off. The filtered product is washed and dried. For this purpose, water in admixture with one of the above-mentioned polar organic solvent can be used.

Examples of polysaccharides to be used in the inventive method, are hydroxyethylcellulose, hydroxyethylmethylcellulose, hydroxypropylcellulose and starch. A further example is dihydroxypropylcellulose. This last term is understood to refer to a cellulose, which has been reacted with glycidol.

The compound of the general formula

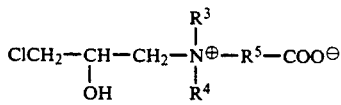

III used in the inventive method, is novel and is claimed within the scope of the present invention as an intermediate for the synthesis of polysaccharides containing the inventive betaine groups.

This compound can be synthesized according to the following reaction scheme:

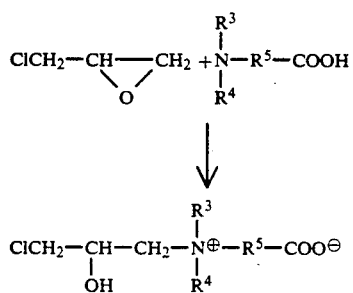

To carry out the reaction, the dialkylamino acid is dissolved in water or suspended in a lower aliphatic alcohol, such as isopropanol. Epichlorohydrin is then added dropwise to the solution or suspension. The reaction temperature is about 40° to 80° C. The reaction time is 2 to 8 hours. The solution obtained can be used directly for carrying out the inventive method without removal of the solvent.

A further aspect of the invention is the use of the novel betaine-containing polysaccharides in cosmetic preparations, especially for the care of hair. The inventive compounds meet the requirements outlined hereinabove particularly well.

The inventive compounds can be processed together with anionic surfactants without any cloudiness or precipitation being observed. If hair is treated with aqueous preparations of the inventive compounds, it develops the desired gloss and a pleasant, supple, soft handle and is readily combable. The products have proven to be useful especially for the care of damaged hair.

The inventive compounds are then contained in the aqueous solutions in an amount of 0.1 to 2.5% by weight. Skin irritations or hair damage have not been observed with the inventive compounds.

The inventive compounds can, moreover, be used to thicken aqueous solutions or aqueous suspensions. They are suitable for the treatment of textile fibers or of yarns produced therefrom or sheet-like textile fabrics. A considerable improvement in the handle and a decrease in the electrostatic charge is obtained in this manner. The inventive compounds can furthermore be added during the manufacture of paper or paper pulp. The compounds can furthermore be used to thicken aqueous vehicles or binders.

In the following examples, the synthesis of inventive compounds is shown. It should be noted that these examples are given by way of illustration and not by way of limitation. Furthermore, the application properties of the compounds are shown in comparison with those of products of the state of the art.

I PREPARATION OF INVENTIVE BETAINIC MODIFYING AGENTS

1. To 27.1 g of dimethylglycine and 102 g of water, 23.2 g of epichlorohydrin are added dropwise with stirring at 50° C. within 2 hours. As the reaction progresses, the system, which initially consists of 2 phases, becomes clear. After 2 hours, the epichlorohydrin is consumed, the content, as determined by gas chromatography, being less than 0.02% by weight. For recording a $^1$H-NMR spectrum, a portion of the product is freed from solvent. Characteristic signals in the $^1$H-NMR spectrum, recorded in d-DMSO, are the peak of the methyl groups at the quaternary nitrogen atom at $\delta = 3.2$ ppm and the peak of the methyl groups at the not quaternized nitrogen atom of the unreacted dimethylglycine at $\delta = 2.6$ ppm. From the intensity ratio of these signals, it can be concluded that, based on the dimethylglycine used, a yield of 54% of the internal salt of N-(3-chloro-2-hydroxypropyl)-N-(carboxymethyl)-N,N-dimethylammonium hydroxide of Formula IIIa, on the basis of the dimethylglycine used, is obtained.

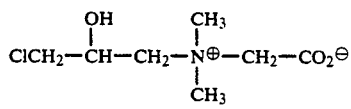

IIIa

2. To 27.1 g of dimethylglycine and 27.1 g of isopropanol, 23.2 g of epichlorohydrin are added dropwise with stirring at 50° C. within 2 hours. The dimethylglycine, initially present in suspended form, goes into solution after about 2 hours with a slightly exothermic reaction. The temperature is maintained at 50° C. The total reaction time after the addition of the epichlorohydrin is 4 hours. The epichlorohydrin content has then fallen to less than 0.02% by weight. For recording a $^1$H-NMR spectrum, a portion of the product is freed from solvent. The characteristic signals of the methyl substituents at the nitrogen are evaluated quantitatively as in Example 1. The yield is found to be 87%, based on dimethylglycine, of the internal salt of N-(3-chloro-2-hydroxypropyl)-N-(carboxymethyl)-N,N-dimethylammonium hydroxide of formula IIIa (compare Section I 1.). The solution of the zwitterionic modifying agent, ready for use, contains 65% solids.

3. To 13.5 g of 11-dimethylaminoundecanoic acid and 37.8 g of isopropanol, 5.2 g of epichlorohydrin are added dropwise with stirring at 50° C. within 2 hours. The reaction temperature is maintained for 4 hours. After that time, the epichlorohydrin content has fallen to less than 0.1% by weight. To determine the yield with the help of a $^1$H-NMR spectrum, the method given in Section I 1. is followed. The yield is found to be 72% of the internal salt of N-(3-chloro-2-hydroxypropyl)-N-(10-carboxydecyl)-N,N-dimethylammonium hydroxide of the formula IIIb

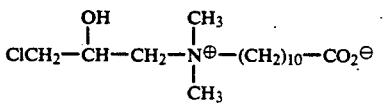

IIIb based on the 11-dimethylaminoundecanoic acid. The solution of the zwitterionic modifying agent, ready for use, contains 33% solids. 4. To 14.4 g of 3-dimethylamino-2,2-dimethylpropionic acid and 59.3 g of isopropanol, 9.2 g of epichlorohydrin are added dropwise with stirring at 50° C. within 2 hours. The reaction conditions are maintained for a further 6 hours. After that time, the epichlorohydrin has been consumed with the exception of 0.25% by weight in the reaction mixture. To determine the yield with the help of a $^1$H-NMR spectrum, the method of Section I 1. is followed. A yield of 82% of the internal salt of N-(3-chloro-2-hydroxypropyl)-N-(2-carboxy-2,2-dimethylpropyl)-N,N-dimethylammonium hydroxide of formula IIIc

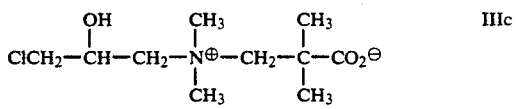

based on the 3-dimethylamino-2,2-dimethylpropionic acid, is obtained. The zwitterionic modifying agent, ready for used, contains 28.5% solids.

5. To 43.1 g of N-butyl-N-methylaminoacetic acid and 189.4 g of isopropanol, 27.5 g of epichlorohydrin are added dropwise with 2 hours at 50° C. The reactions conditions are maintained for a further 6 hours. After that time, the epichlorohydrin content has fallen to 0.01% by weight. For the determination of the yield with the help of a $^1$H-NMR spectrum, the method of Section I 1. is followed. A yield of 72% of the internal salt of N-(3-chloro-2-hydroxypropyl)-N-(carboxymethyl)-N-butyl-N-methylammonium hydroxide of Formula IIId

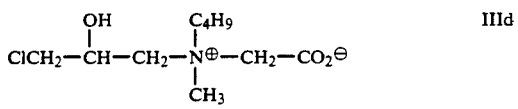

based on the N-butyl-N-methylaminoacetic acid, is obtained. The zwitterionic modifying agent, ready for used, contains 27% solids.

II PREPARATION OF THE INVENTIVE POLYSACCHARIDES WITH BETAINE GROUPS

1. Commercial hydroxyethylcellulose (25 g), a 2% solution of which has a Brookfield viscosity of 6,000 mPas, is suspended in 160 mL of acetone, mixed at room temperature with 7.4 g 40% of sodium hydroxide solution and subsequently stirred for 30 minutes at room temperature. Over a period of 15 minutes, 19.2 g of the ready for use solution of the modifying agent of Section I 2., together with 7 g of water, are added dropwise at 40° C. The reaction mixture is stirred for 8 hours at 40° C. Subsequently, it is treated with 9 g of acetic acid, cooled and filtered. The modified cellulose is washed with a mixture of 90 parts of acetone and 10 parts of water and subsequently with pure acetone and dried at 50° C. and 60 mbar to constant weight. The nitrogen content is determined to be 2.2%. The Brookfield viscosity of a 2% aqueous solution of the cellulose betaine is 300 mPas.

2. Commercial hydroxyethylcellulose (25 g), a 2% solution of which has a Brookfield viscosity of 15,000 mPas, is suspended in 160 mL of acetone, mixed at room temperature with 7.4 g 40% of sodium hydroxide solution and subsequently stirred for 30 minutes at room temperature. Over a period of 15 minutes, 19.2 g of the ready for use solution of the modifying agent of Section I 2., together with 7 g of water, are added dropwise at 40° C. The reaction mixture is stirred for 8 hours at 40° C. Subsequently, it is treated with 9 g of acetic acid, cooled and filtered. The modified cellulose is washed with a mixture of 90 parts of acetone and 10 parts of water and subsequently with pure acetone and dried at 50° C. and 60 mbar to constant weight. The nitrogen content is determined to be 2.2%. The Brookfield viscosity of a 2% aqueous solution of the cellulose betaine is 1,800 mPas.

3. Commercial hydroxyethylcellulose (13 g), a 2% solution of which has a Brookfield viscosity of 40,000 mPas, is suspended in 85 mL of acetone, mixed at room temperature with 3.9 g 40% of sodium hydroxide solution and subsequently stirred for 30 minutes at room temperature. Over a period of 15 minutes, 35 g of the ready for use solution of the modifying agent of Section I 3. are added dropwise at 50° C. The reaction mixture is stirred for 4 hours at 50° C. Subsequently, it is treated with 4.5 g of acetic acid, cooled and filtered. The modified cellulose is washed with a mixture of 90 parts of acetone and 10 parts of water and subsequently with pure acetone and dried at 50° C. and 60 mbar. The nitrogen content is 0.5%.

4. Commercial hydroxyethylcellulose (19 g), a 2% solution of which has a Brookfield viscosity of 40,000 mPas, is suspended in 200 mL of acetone, mixed at room temperature with 5.6 g 40% of sodium hydroxide solution and subsequently stirred for 30 minutes at room temperature. Over a period of 15 minutes, 30 g of the ready for use solution of the modifying agent of Section I 4. are added dropwise at 50° C. The reaction mixture is stirred for 4 hours at 50° C. Subsequently, it is treated with 6.5 g of acetic acid, cooled and filtered. The modified cellulose is washed with a mixture of 90 parts of acetone and 10 parts of water and subsequently with pure acetone and dried at 50° C. and 60 mbar. The nitrogen content is 1.6%.

5. Commercial hydroxyethylcellulose (16.2 g), a 2% solution of which has a Brookfield viscosity of 40,000 mPas, is suspended in 100 mL of acetone, mixed at room temperature with 4.8 g 40% of sodium hydroxide solution and subsequently stirred for 30 minutes at room temperature. Over a period of 15 minutes, 7.5 g of the ready for use solution of the modifying agent of Section I 5., together with 4.5 g of water, are added dropwise at 50° C. The reaction mixture is stirred for 4 hours at 50° C. Subsequently, it is treated with 5.8 g of acetic acid, cooled and filtered. The modified cellulose is washed with a mixture of 90 parts of acetone and 10 parts of water and subsequently with pure acetone and dried at 50° C. and 60 mbar. The nitrogen content is 1.0%.

6. Soluble starch (26 g) is suspended in 135 mL of isopropanol, mixed at room temperature with 3.9 g 40% of sodium hydroxide solution and subsequently stirred for 30 minutes at room temperature. Over a period of 15 minutes, 16.5 g of the ready for use solution of the modifying agent of Section I 2. are added dropwise at 50° C. The reaction mixture is stirred for 4 hours at 50° C. Subsequently, it is treated with 3.1 g of acetic acid, cooled and filtered. The modified cellulose is washed with a mixture of 90 parts of isopropanol and 10 parts of water and subsequently with pure isopropanol and dried at 50° C. and 60 mbar. The nitrogen content is 0.4%.

7. Bleached beech sulfite pulp (moderate viscosity) is comminuted to particles with a maximum fiber length of about 1 mm. A glass apparatus is equipped with an intensive condenser and a dropping funnel, the temperature of which can be controlled. The intensive condenser and the dropping funnel are operated at −15° C. with the help of a Kryomat. In this glass apparatus, 34.3 g of the comminuted beech sulfite pulp are suspended in 650 mL of solvent, consisting of 85 parts of isopropanol and 15 parts of water, and stirred for 30 minutes at room temperature. The suspension is mixed with 45.3 mL of 20% sodium hydroxide solution and stirred for a further 45 minutes at room temperature. Thereupon 33.6 g of ethylene oxide are added dropwise within 20 minutes. The batch is subsequently heated to 50° C. and kept for 2 hours at this temperature. After that, at the same temperature, a ready for use solution of the zwitterionic modifying agents of Section I 2. is added dropwise within 20 minutes. In the further course of the reaction, stirring is carried out for 2 hours at 60° C., after which the temperature is raised to 75° C. and the mixture is treated with 15 g of acetic acid. The cooled product is filtered off, washed with 600 mL of isopropanol/water (85/15) and subsequently with isopropanol. After drying at 50° C. and 60 mbar, 100 g of a zwitterionic modified cellulose ether are obtained. The product has a nitrogen content of 2.4%.

8. Cellulose powder (32 g) for chromatography is suspended in 420 mL acetone and mixed with 55 g of 20% sodium hydroxide solution. The suspension obtained is stirred for 30 minutes at room temperature. Subsequently, 41.2 g of 2,3-epoxypropan-1-ol is added dropwise at 60° C. within 20 minutes. Subsequently, 56 g of the modifying agent of Section ! 2. are added dropwise at the same temperature. The batch is stirred for a further 15 minutes at the same temperature. After cooling, the product is isolated by filtration, washed with acetone/water (90/10) and with acetone and finally dried at 50° C. and 60 mbar. The zwitterionic modified cellulose ether obtained contains 2.4% nitrogen.

9. Commercial hydroxypropylcellulose (25 g), a 2% solution of which has a Brookfield viscosity of 5,000 mPas, is suspended in 125 mL of water at a temperature of 60° C. and mixed with 7.4 g of 40% sodium hydroxide solution. Subsequently, 19.5 g of the zwitterionic modifying agent of Section I 2. are added. The batch is stirred for 3 hours at the same temperature. Subsequently, it is mixed with 9 mL of glacial acetic acid and filtered hot. The product is washed several times with warm (60° C.) water and dried at 60° C. and 60 mbar. The zwitterionic modified hydroxypropylcellulose has a nitrogen content of 0.5%.

10. Commercial methylhydroxyethylcellulose (25 g), the 2% solution of which has a Hoeppler viscosity of 4,000 mPas, is suspended in 140 mL of acetone, mixed with 6.4 g of 40% sodium solution and stirred for 30 minutes at room temperature. Subsequently, 16.7 g of the zwitterionic modifying agent of Section I 2. is added dropwise within 20 minutes at room temperature. The batch is stirred for 5 hours at 50° C. After that, 4 mL of acetic acid are added. After cooling, the cellulose ether is filtered off, washed with acetone/water (90/10) and acetone and dried at 50° C. and 60 mbar. The zwitterionic cellulose ether has a nitrogen content of 2%.

III PREPARATION OF CELLULOSE ETHER WITH CATIONIC AND ANIONIC GROUPS, WHICH IS NOT OF THE INVENTION. THE PRODUCT CORRESPONDS TO U.S. Pat. No. 3,472,840. NO DIRECTIONS ARE GIVEN THERE FOR PREPARING THE PRODUCT.

Commercial hydroxyethylcellulose (25 g), a 2% solution of which has a Brookfield viscosity of 15,000 mPas, is suspended in 160 mL of acetone, mixed with 12.5 g of a 40% sodium hydroxide solution and stirred for 30 minutes at room temperature. Subsequently, 23 g of a 50% aqueous solution of 3-chloro-2-hydroxypropyl-trimethylammonium chloride are added dropwise within 15 minutes. Subsequently, the temperature is raised to 50° C. and stirring is continued at this temperature for 2 hours. Thereupon, 7.2 g of sodium monochloroacetate are added at a temperature raised to 60° C. The batch is stirred for a further 2.5 hours at this temperature. After cooling, the product is filtered off, washed with acetone/water (90/10) and acetone and dried at 50° C. and 60 mbar. The modified cellulose ether has a nitrogen content of 1.9%.

IV THICKENING AQUEOUS SURFACTANT SOLUTIONS

In this example, the thickening effect of a cellulose betaine in surfactant solutions and the compatibility of these cellulose betaines with anionic as well as with cationic surfactants is shown. For comparison, solutions with cellulose betaines of the state of the art are prepared. The cationic and anionic modified cellulose ether corresponds to U.S. Pat. No. 3,472,840. Its preparation is described in Section III. It does not dissolve completely in water and its solution is not clear. A cellulose betaine, which was prepared according to the Japanese Offenlegungsschrift 80-43 165 (Example 1), is not completely soluble in and does not form a clear solution is sodium lauryl sulfate solutions. The inventive cellulose betaine, the preparation of which is described in Section II 2, is soluble in aqueous solutions of sodium lauryl sulfate and dodecyldimethylbenzylammonium chloride and does form a clear solution.

This cellulose betaine is added to surfactant solutions of different concentrations, so that the resulting solutions contain cellulose betaine at a concentration of 1%. The viscosities are measured with a Contraves Rheomat 115 at a constant shear gradient of $D=167.2$ s$^{-1}$. The viscosities of the pure surfactant solutions fall within the range of 5 to 11 mPas. The results are summarized in the following Table.

| Thickening of Sodium Lauryl Sulfate Solutions | | Thickening of Dodecyldimethylbenzyl-ammonium Chloride Solutions | |
|---|---|---|---|
| Surfactant Concentration % by weight | Viscosity [mPas] | Surfactant Concentration % by weight | Viscosity [mPas] |
| 1 | 34. | 1 | 43.7 |
| 2 | 37.5 | 2 | 58 |
| 5 | 49.7 | 5 | 56.3 |
| 7.5 | 73 | 7.5 | 68 |
| 10 | 77 | 10 | 69.3 |
| 15 | 113.7 | 15 | 84.3 |

V APPLICATION TESTS-HAIR CONDITIONING

1. Dressing hair with inventive betainic cellulose derivatives and betainic and cationic cellulose derivatives of the state of the art.

The following cellulose derivatives are investigated with respect to their conditioning effect on hair:

A: A hydroxyethylcellulose, modified with 3-chloro-2-hydroxypropyltrimethylammonium chloride and corresponding to U.S. Pat. No. 3,472,840. The product has a nitrogen content of 1.7%.

B: A hydroxyethylcellulose, which is modified with 3-chloro-2-hydroxypropyltrimethylammonium chloride and sodium chloroacetate and corresponds to U.S. Pat. No. 3,472,840 and the preparation of which is described in Section III of this document.

C: A hydroxyethylcellulose, modified with 2-chloroethyldiethylamine and sodium chloroacetate and corresponding to Example 1 of the Japanese Offenlegungsschrift 80-43 165.

D: An inventive cellulose derivative with betaine groups. The synthesis is described in Section II 2.

E: An inventive cellulose derivative with betaine groups. The synthesis is described in Section II 8.

Chinese fine hair, 15 cm long, is bleached with a commercial bleach for 1 hour according to the directions provided and subsequently dried. The care rinse, enclosed with the bleaching agent, is not used. The now lightened and damaged hair is tied into strands of about 1 g each. The strands are left for 10 minutes at 30° C. in the solutions described above. Subsequently, they are rinsed thoroughly for 3 minutes in lukewarm running water, dried 12 hours in air and combed. In each case, 3 strands of hair are treated with each of the solutions.

With regard to handle and combability, there are clear differences between the differently treated strands of hair. On the basis of these differences, the cellulose derivatives A to D can be arranged in a sequence. The cellulose derivatives, which lead to the best result, are named first. The sequence is determined to be:

D>B>E>A>C>bleached untreated hair.

D an E are cellulose derivatives of the invention.

2. Treatment of hair with shampoo preparations, which contain betainic cellulose derivatives of the invention and betainic and cationic cellulose derivatives of the state of the art.

With the cellulose derivatives A, B, C, D, and E, described under V 1., shampoo preparations are produced, which consist of 1% cellulose derivative, 20% sodium lauryl sulfate, 4% sodium chloride and 75% water. In addition, a shampoo preparation, consisting of 20% sodium lauryl sulfate, 4% sodium chloride and 76% water, is produced for comparison.

Chinese fine hair is bleached and tied as described.

In each case, one strand of hairs is moistened under luke-warm, running water. The wet hair is washed for 10 minutes with a pea-size amount of the respective shampoo preparation, then rinsed thoroughly with lukewarm, running water and dried with the hair drier. In each case, 3 hair strands are treated in the manner described with each of the shampoo preparations.

There are clear differences with respect to handle and combability. On the basis of the results, the cellulose derivatives can be arranged in the following order:

D>E>C>B>A>shampoo without cellulose derivatives.

D and E are cellulose derivatives of the invention.

We claim:

1. A betaine group-containing polysaccharide with recurring anhydroglucose units of the formula

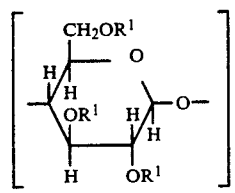

in which the $R^1$ groups are the same or different and represent methyl, $(C_nH_{2n}O)_mR^2$ or

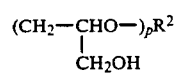

wherein n=2 or 3, m=0 to 10, p=0 to 10 and $R^2$ is a hydrogen atom or the betaine group

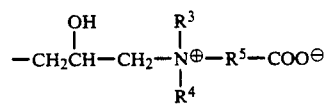

in which
$R^3$ and $R^4$ are the same or different and represent an alkyl group with 1 to 4 carbon atoms and
$R^5$ is a divalent aliphatic hydrocarbon group with 1 to 10 carbon atoms, with the proviso that at least 0.5% of the $R^1$ groups in the polysaccharide molecule represent the betaine group.

2. The polysaccharide of claim 1, wherein 5 to 20% of the $R^1$ groups represent a betaine group.

3. The polysaccharide of claims 1 or 2, wherein n=2, m=0 to 10 and p=0.

4. A method for the synthesis of a betaine group-containing polysaccharide, which comprises
(a) suspending in a polar organic solvent a polysaccharide with recurring anhydroglucose units of the formula

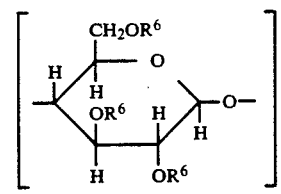

in which the $R^6$ groups are the same or different and represent $CH_3$, $(C_nH_{2n}O)_mH$ or

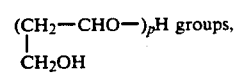

groups, wherein n=2 or 3, m=0 to 10 and p=0 to 10, with the proviso that not more than 70% of the sum of the $R^6$ groups are methyl groups.
(b) adding to the suspension at least 0.1 to 3 molar amounts of sodium hydroxide, based on anhydroglucose units,
(c) permitting the alkaline suspension thus obtained to stand for about between 10 to 120 minutes at 0° to 30° C.,
(d) adding, based on the anhydroglucose units, 0.1 to 3 molar amounts of the compound

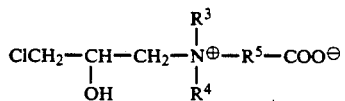

in which
$R^3$ and $R^4$ are the same or different and represent an alkyl group with 1 to 4 carbon atoms and
$R^5$ is a divalent aliphatic hydrocarbon group with 1 to 10 carbon atoms, said compound being dissolved in water or a polar organic solvent,
(e) permitting the mixture thus obtained to react at temperatures of between about 30° to 80° C. with stirring for 0.5 to 12 hours, and
(f) upon completion of the reaction, isolating the product obtained by filtration, washing and drying.

5. The method of claim 4, wherein the polysaccharide is suspended in step (a) in the solvent in such amounts that a suspension containing 1 to 25% by weight of solids is obtained.

6. The method of claims 4 or 5, wherein 0.5 to 1.5 molar amounts of sodium hydroxide, based on anhydroglucose unit, is added to the suspension in step (b).

7. The method of claim 4, wherein in step (b) sodium hydroxide is added in the form of an aqueous solution.

8. The method of claim 4, wherein the polar organic solvent of step (a) contains water.

9. The method of claim 4, wherein the alkaline suspension is stirred during step (c).

10. The method of claim 4, wherein the polar organic solvent of step (d) comprises water.

11. The method of claim 4, wherein, prior to step (f), the reaction mixture is neutralized.

12. A hair care preparation comprising an aqueous vehicle and an effective amount of the polysaccharide of claims 1 or 2.

13. The preparation of claim 12, wherein said effective amount of said polysaccharide is between about 0.1 to 2.5% by weight.

14. A hair care preparation essentially consisting of the preparation of claim 13.

* * * * *